(12) United States Patent
Seki et al.

(10) Patent No.: US 6,380,148 B2
(45) Date of Patent: Apr. 30, 2002

(54) AZEOTROPIC MIXTURE OF PERFLUOROALKYL IODIDE AND HYDROGEN FLUORIDE, AND METHOD FOR ISOLATING AND PURIFYING PERFLUOROALKYL IODIDES

(75) Inventors: Eiji Seki; Tatsuya Otsuka; Tatsuya Hirata; Yoshinori Tanaka; Hirokazu Aoyama, all of Settsu (JP)

(73) Assignee: Daikin Industries, Osaka (JP)

( * ) Notice: Subject to any disclaimer, the term of this patent is extended or adjusted under 35 U.S.C. 154(b) by 0 days.

(21) Appl. No.: 09/886,270

(22) Filed: Jun. 22, 2001

Related U.S. Application Data

(62) Division of application No. 09/445,584, filed as application No. PCT/JP98/02351 on May 27, 1998, now Pat. No. 6,271,189.

(30) Foreign Application Priority Data

Jun. 13, 1997 (JP) ............................................... 9-156709

(51) Int. Cl.$^7$ .................................................. C11D 7/30
(52) U.S. Cl. ........................ 510/408; 510/412; 510/415
(58) Field of Search ................................ 510/408, 412, 510/415

(56) References Cited

U.S. PATENT DOCUMENTS 4,118,290 A * 10/1978 Semmler et al. .......... 204/59 F
5,481,028 A   1/1996 Petrov et al.

FOREIGN PATENT DOCUMENTS

| JP | 9-500900 | 1/1997 |
| WO | WO 97/03936 | 2/1997 |
| WO | WO 97/07052 | 2/1997 |

* cited by examiner

*Primary Examiner*—Charles Boyer
(74) *Attorney, Agent, or Firm*—Larson & Taylor PLC

(57) ABSTRACT

The present invention provides a method for isolating and purifying 1,1,1,2,2-pentafluoroethyl iodide or hydrogen fluoride from a mixture of 1,1,1,2,2-pentafluoroethyl iodide and hydrogen fluoride, characterized by distilling an azeotropic mixture of 1,1,1,2,2-pentafluoroethyl iodide and hydrogen fluoride from a mixture containing 1,1,1,2,2-pentafluoroethyl iodide and hydrogen fluoride either after liquid—liquid separation when the mixture is heterogeneous or directly when the mixture is homogeneous to obtain 1,1,1,2,2-pentafluoroethyl iodide or hydrogen fluoride from the bottom of the distillation column.

4 Claims, 2 Drawing Sheets

Liquid-Liquid Equilibrium

AZEOTROPIC MIXTURE OF PERFLUOROALKYL IODIDE AND HYDROGEN FLUORIDE, AND METHOD FOR ISOLATING AND PURIFYING PERFLUOROALKYL IODIDES

This application is a divisional of 09/445,584 filed Dec. 13, 1999 now U.S. Pat. No. 6,271,189 which is a 371 of PCT/JP98/02351 filed May 27, 1998.

FIELD OF THE INVENTION

The present invention relates to a novel azeotropic mixture of hydrogen fluoride and 1,1,1,2,2-pentafluoroethyl iodide and a method for isolating and purifying 1,1,1,2,2-pentafluoroethyl iodide or hydrogen fluoride from a mixture containing 1,1,1,2,2-pentafluoroethyl iodide and hydrogen fluoride.

BACKGROUND ART 1,1,1,2,2-Pentafluoroethyl iodide is a compound useful as an intermediate for a repellent, an etchant, a surface modifier, a pharmaceutical, an agricultural substance or the like and is used for various applications.

In these applications, for example, when 1,1,1,2,2-pentafluoroethyl iodide as the raw material is reacted with hydrogen fluoride, or when hydrogen fluoride is produced as a by-product in producing 1,1,1,2,2-pentafluoroethyl iodide, or when 1,1,1,2,2-pentafluoroethyl iodide is produced using hydrogen fluoride, there is formed a mixture containing 1,1,1,2,2-pentafluoroethyl iodide and hydrogen fluoride in a variable ratio.

To purify 1,1,1,2,2-pentafluoroethyl iodide by separating hydrogen fluoride from such mixture, generally hydrogen fluoride is eliminated as an aqueous solution of hydrofluoric acid, e.g. by washing with water or with alkaline solution. However, in the method of removing hydrogen fluoride by washing, unavoidably hydrogen fluoride is discarded entirely as an aqueous solution. Thus the method raises problems that hydrogen fluoride is uselessly thrown away and the method incurs costs for washing and dumping.

DISCLOSURE OF THE INVENTION

It is a principal object of the present invention to provide a method for efficiently isolating and purifying perfluoroalkyl iodide or hydrogen fluoride from a mixture containing 1,1,1,2,2-pentafluoroethyl iodide and hydrogen fluoride without washing.

The present inventors carried out extensive research in view of the foregoing problems and newly found that a mixture of 1,1,1,2,2-pentafluoroethyl iodide and hydrogen fluoride forms a minimum azeotropic mixture and that 1,1,1,2,2-pentafluoroethyl iodide and hydrogen fluoride have a low mutual solubility. It was also discovered that utilizing such properties, 1,1,1,2,2-pentafluoroethyl iodide or hydrogen fluoride can be efficiently isolated and purified from a mixture containing 1,1,1,2,2-pentafluoroethyl iodide and hydrogen fluoride by distilling off said azeotropic mixture either directly when the mixture is homogeneous or after liquid—liquid separation when the mixture is heterogeneous. Based on these findings, the present invention was completed.

That is, the present invention provides the following azeotropic mixtures and isolating and purifying methods.
(1) An azeotropic mixture consisting of hydrogen fluoride and 1,1,1,2,2-pentafluoroethyl iodide.

(2) The azeotropic mixture as defined above in item (1) which comprises 86 to 88% by weight of 1,1,1,2,2-pentafluoroethyl iodide and 12 to 14% by weight of hydrogen fluoride under an atmospheric pressure.

(3) A method for isolating and purifying 1,1,1,2,2-pentafluoroethyl iodide or hydrogen fluoride from a mixture containing 1,1,1,2,2-pentafluoroethyl iodide and hydrogen fluoride, characterized by conducting liquid—liquid separation of a heterogeneous mixture containing 1,1,1,2,2-pentafluoroethyl iodide and hydrogen fluoride and distilling a layer of 1,1,1,2,2-pentafluoroethyl iodide or a layer of hydrogen fluoride so that an azeotropic mixture of 1,1,1,2,2-pentafluoroethyl iodide and hydrogen fluoride is removed through the top of a distillation column while 1,1,1,2,2-pentafluoroethyl iodide or hydrogen fluoride is obtained from the bottom of the distillation column.

(4) A method for isolating and purifying 1,1,1,2,2-pentafluoroethyl iodide or hydrogen fluoride from a mixture containing 1,1,1,2,2-pentafluoroethyl iodide and hydrogen fluoride, characterized by distilling a homogeneous mixture containing 1,1,1,2,2-pentafluoroethyl iodide and hydrogen fluoride so that an azeotropic mixture of 1,1,1,2,2-pentafluoroethyl iodide and hydrogen fluoride is removed through the top of a distillation column while 1,1,1,2,2-pentafluoroethyl iodide or hydrogen fluoride is obtained from the bottom of the distillation column.

(5) A method for isolating and purifying 1,1,1,2,2-pentafluoroethyl iodide or hydrogen fluoride from a mixture containing 1,1,1,2,2-pentafluoroethyl iodide and hydrogen fluoride, characterized by conducting a liquid—liquid separation of the distillate obtained through the top of the distillation column by the method as defined above in item (3) or (4), and distilling a layer of 1,1,1,2,2-pentafluoroethyl iodide or a layer of hydrogen fluoride so that an azeotropic mixture of 1,1,1,2,2-pentafluoroethyl iodide and hydrogen fluoride is removed through the top of a distillation column while 1,1,1,2,2-pentafluoroethyl iodide or hydrogen fluoride is obtained from the bottom of the distillation column.

1,1,1,2,2-Pentafluoroethyl iodide and hydrogen fluoride form a minimum azeotropic mixture in proportions of 86 to 88% by weight of the former and 12 to 14% by weight of the latter under an atmospheric pressure. It is unknown, i.e. a novel finding that these two compounds give a minimum azeotropic mixture.

1,1,1,2,2-pentafluoroethyl iodide and hydrogen fluoride have a limited mutual solubility and are easily separable into two layers. Each of the separated layers contains only a small amount of other component.

The methods of the present invention are based on the newly discovered properties of a mixture of 1,1,1,2,2-pentafluoroethyl iodide and hydrogen fluoride. When the mixture is homogeneous, it is used as such. Alternatively, when the mixture is heterogeneous, a liquid—liquid separated product is used. In either case, distillation is carried out to remove an azeotropic mixture thereof, whereby 1,1,1,2,2-pentafluoroethyl iodide or hydrogen fluoride can be efficiently isolated and purified from the mixture thereof.

Separation methods differ depending on whether a mixture of 1,1,1,2,2-pentafluoroethyl iodide and hydrogen fluoride is heterogeneous or homogeneous and are separately described below.

First, when the mixture of 1,1,1,2,2-pentafluoroethyl iodide and hydrogen fluoride is heterogeneous, the mixture is subjected to liquid—liquid separation, and a layer of 1,1,1,2,2-pentafluoroethyl iodide is distilled to remove an azeotropic mixture through the top of a distillation column, whereby 1,1,1,2,2-pentafluoroethyl iodide substantially free of hydrogen fluoride can be efficiently obtained from the bottom of the distillation column. In this case, when a layer of hydrogen fluoride obtained by liquid—liquid separation is distilled to remove an azeotropic mixture through the top of the distillation column, hydrogen fluoride substantially free of 1,1,1,2,2-pentafluoroethyl iodide can be efficiently obtained from the bottom of the distillation column.

Further, when the distillate obtained through the top of the distillation column is subjected to the same procedure as above after liquid—liquid separation, hydrogen fluoride substantially free of 1,1,1,2,2-pentafluoroethyl iodide or 1,1,1,2,2-pentafluoroethyl iodide substantially free of hydrogen fluoride can be obtained.

When a mixture of 1,1,1,2,2-pentafluoroethyl iodide and hydrogen fluoride is homogeneous and contains a small amount of 1,1,1,2,2-pentafluoroethyl iodide, the mixture is distilled as such to remove an azeotropic mixture from the top of the distillation column, whereby hydrogen fluoride substantially free of 1,1,1,2,2-pentafluoroethyl iodide can be efficiently obtained from the bottom of the distillation column. On the other hand, when a mixture of 1,1,1,2,2-pentafluoroethyl iodide and hydrogen fluoride is homogeneous and contains a small amount of hydrogen fluoride, the mixture is distilled as such to remove an azeotropic mixture from the top of the distillation column, whereby 1,1,1,2,2-pentafluoroethyl iodide substantially free of hydrogen fluoride can be efficiently obtained from the bottom of the distillation column.

Further, in either case of the mixture containing a small amount of 1,1,1,2,2-pentafluoroethyl iodide or containing a small amount of hydrogen fluoride, hydrogen fluoride substantially free of 1,1,1,2,2-pentafluoroethyl iodide or 1,1,1,2,2-pentafluoroethyl iodide substantially free of hydrogen fluoride can be obtained by subjecting the distillate obtained through the top of a distillation column to the same procedure as above after liquid—liquid separation.

According to the method of the present invention, the following advantage is given. Even when a mixture containing 1,1,1,2,2-pentafluoroethyl iodide and hydrogen fluoride contains other component, an azeotropic mixture of 1,1,1,2,2-pentafluoroethyl iodide and hydrogen fluoride is formed by distillation, so that 1,1,1,2,2-pentafluoroethyl iodide and hydrogen fluoride can be easily isolated even in the presence of other component. For example, even if the mixture contains a catalyst used for the reaction, reactants, a higher boiling reaction intermediate, reaction product and the like, 1,1,1,2,2-pentafluoroethyl iodide and hydrogen fluoride substantially free of these components can be easily obtained.

While the methods of the present invention are described above as batchwise methods, continuous rectification is feasible by combining the similar methods.

There is no limitation on the type of distillation columns. The distillation column may be integral with a reactor. The operating pressure is not limited, but generally in the range of about 1 to about 30 kg/cm$^2$G.

EFFECT OF THE INVENTION

According to the present invention, 1,1,1,2,2-pentafluoroethyl iodide or hydrogen fluoride can be efficiently isolated and purified from a mixture containing 1,1,1,2,2-pentafluoroethyl iodide and hydrogen fluoride without washing by a simple procedure of distilling off an azeotropic mixture thereof.

BEST MODE OF CARRYING OUT THE INVENTION

The present invention is described below in more detail with reference to the following examples.

EXAMPLE 1

Figure 1:
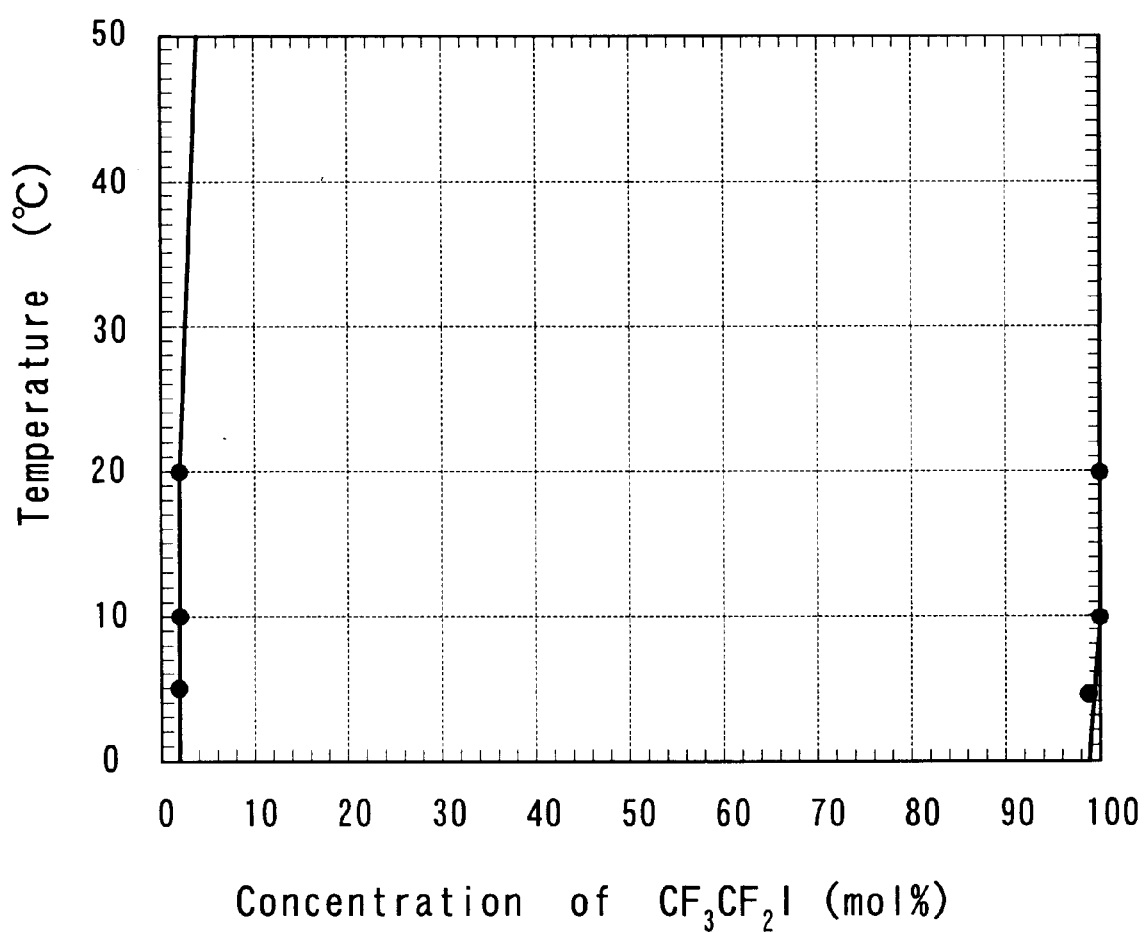
FIG. 1 is a graph showing a liquid—liquid equilibrium of 1,1,1,2,2-pentafluoroethyl iodide and hydrogen fluoride.

Solubility of 1,1,1,2,2-pentafluoroethyl Iodide and HF 1,1,1,2,2-pentafluoroethyl iodide and hydrogen fluoride were placed into a PFA tube in predetermined proportions and were maintained at a specific temperature. After the solubility reached an equilibrium, the proportions of 1,1,1,2,2-pentafluoroethyl iodide and hydrogen fluoride in a phase of 1,1,1,2,2-pentafluoroethyl iodide and a phase of hydrogen fluoride, respectively were determined. Table 1 and FIG. 1 below show the concentrations (mole %) of 1,1,1,2,2-pentafluoroethyl iodide and hydrogen fluoride in the phase of 1,1,1,2,2-pentafluoroethyl iodide and the phase of hydrogen fluoride, respectively.

TABLE 1

| Temperature | Mutual solubility of $CF_3CF_2I$/HF | |
|---|---|---|
| | Solubility (mole %) | |
| (° C.) | $CF_3CF_2I$/HF | HF/$CF_3CF_2I$ |
| 5 | 1.5–2.5 | 0.11–2.5 |
| 10 | 1.5–2.6 | 0.11–2.5 |
| 20 | 2.0–3.0 | 0.11–2.5 |

EXAMPLE 2

Gas-liquid Equilibrium of 1,1,1,2,2-pentafluoroethyl Iodide and HF 1,1,1,2,2-Pentafluoroethyl iodide and hydrogen fluoride were placed into a bomb in predetermined proportions and were maintained at 40° C. After a gas-liquid distribution reached an equilibrium, the proportions of 1,1,1,2,2-pentafluoroethyl iodide and hydrogen fluoride in each of a liquid phase and a gas phase were determined.

Figure 2:
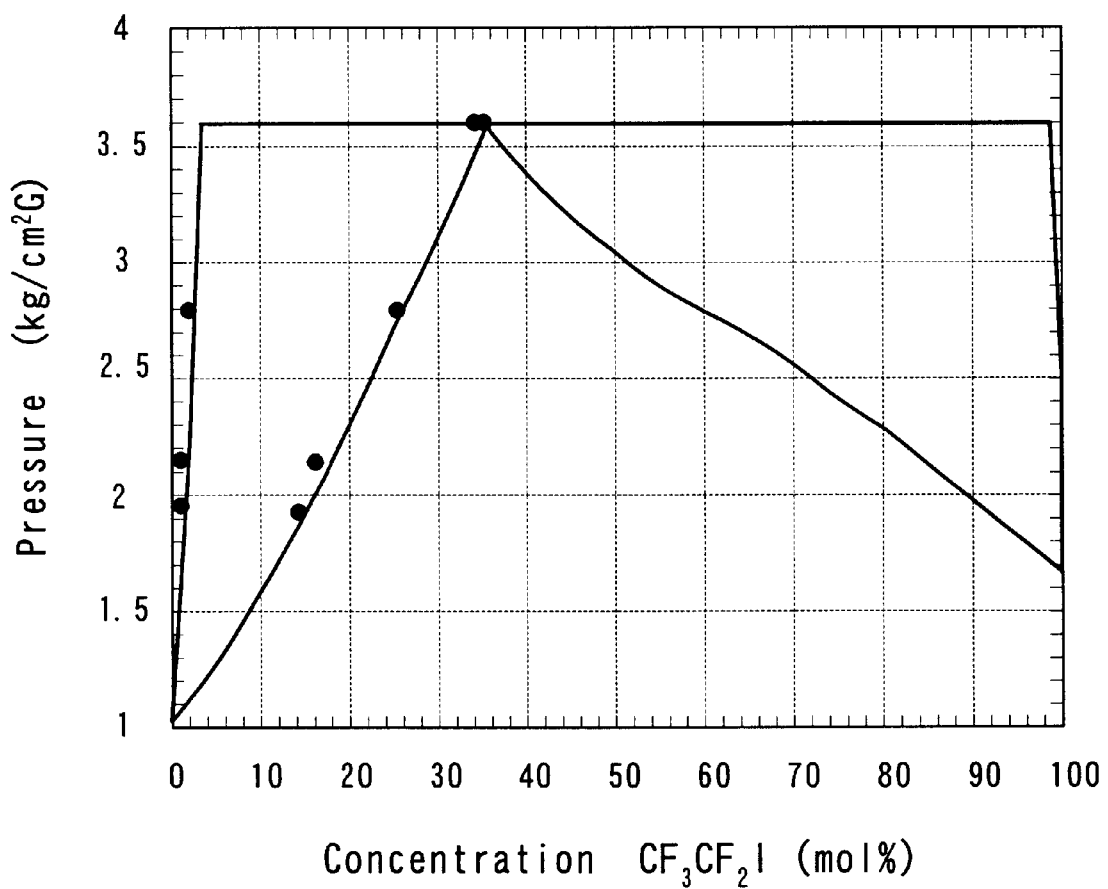
FIG. 2 is a graph showing the concentration of 1,1,1,2,2-pentafluoroethyl iodide in a liquid phase and a gas phase of a mixture of 1,1,1,2,2-pentafluoroethyl iodide and hydrogen fluoride.

Table 2 and FIG. 2 below show the concentration (mole %) of 1,1,1,2,2-pentafluoroethyl iodide in the liquid phase and the gas phase. The graph of FIG. 2 indicates that 1,1,1,2,2-pentafluoroethyl iodide and hydrogen fluoride form an azeotropic mixture. Their composition proportions are 33.3–37.4 mole % of 1,1,1,2,2-pentafluoroethyl iodide and 66.7–62.6 mole % of HF, and their weight ratios are 86–88% by weight of 1,1,1,2,2-pentafluoroethyl iodide and 12–14% by weight of HF.

TABLE 2

Gas-liquid equilibrium of $CF_3CF_2I/HF$

| Liq. phase (mol %) | Gas phase (mol %) | Pressure (kg/cm²G) |
|---|---|---|
| 0.69 | 13.9 | 1.95 |
| 0.8 | 15.5 | 2.15 |
| 0.99 | 24.3 | 2.8 |
| 34.4 | 34.8 | 3.6 |

EXAMPLE 3

Isolation of 1,1,1,2,2-pentafluoroethyl Iodide and HF

A layer of 1,1,1,2,2-pentafluoroethyl iodide (600 g) was withdrawn from a heterogeneous mixture of 1,1,1,2,2-pentafluoroethyl iodide and hydrogen fluoride, and was placed into a distillation apparatus made of SUS 316 (rectification column with an inner diameter 20 mm and a length 120 cm, packing:SULZER laboratory packing, and number of plates:20). The layer was subjected to total reflux under an atmospheric pressure. When the reflux temperature reached in a range of −1.5° C. to −1.2° C., the reflux liquid (130 g) was discharged and 1,1,1,2,2-pentafluoroethyl iodide substantially free of hydrogen fluoride was obtained from the still. On the other hand, when the discharged reflux liquid (130 g) was subjected to liquid—liquid separation, and the obtained layer of 1,1,1,2,2-pentafluoroethyl iodide was distilled in the same manner, 1,1,1,2,2-pentafluoroethyl iodide substantially free of hydrogen fluoride was obtained.

What is claimed is:

1. A method for isolating and purifying 1,1,1,2,2-pentafluoroethyl iodide or hydrogen fluoride from a mixture containing 1,1,1,2,2-pentafluoroethyl iodide and hydrogen fluoride, comprising conducting liquid—liquid separation of a heterogeneous mixture containing 1,1,1,2,2-pentafluoroethyl iodide and hydrogen fluoride and distilling a layer of 1,1,1,2,2-pentafluoroethyl iodide or a layer of hydrogen fluoride so that an azeotropic mixture of 1,1,1,2,2-pentafluoroethyl iodide and hydrogen fluoride is removed through the top of a distillation column while 1,1,1,2,2-pentafluoroethyl iodide or hydrogen fluoride is obtained from the bottom of the distillation column.

2. A method for isolating and purifying 1,1,1,2,2-pentafluoroethyl iodide or hydrogen fluoride from a mixture containing 1,1,1,2,2-pentafluoroethyl iodide and hydrogen fluoride, comprising distilling a homogeneous mixture containing 1,1,1,2,2-pentafluoroethyl iodide and hydrogen fluoride so that an azeotropic mixture of 1,1,1,2,2-pentafluoroethyl iodide and hydrogen fluoride is removed through the top of a distillation column while 1,1,1,2,2-pentafluoroethyl iodide or hydrogen fluoride is obtained from the bottom of the distillation column.

3. A method for isolating and purifying 1,1,1,2,2-pentafluoroethyl iodide or hydrogen fluoride from a mixture containing 1,1,1,2,2-pentafluoroethyl iodide and hydrogen fluoride, comprising conducting a liquid—liquid separation of the distillate obtained through the top of a distillation column by the method as defined above in claim 1, and distilling a layer of 1,1,1,2,2-pentafluoroethyl iodide or a layer of hydrogen fluoride so that an azeotropic mixture of 1,1,1,2,2-pentafluoroethyl iodide and hydrogen fluoride is removed through the top of a distillation column while 1,1,1,2,2-pentafluoroethyl iodide or hydrogen fluoride is obtained from the bottom of the distillation column.

4. A method for isolating and purifying 1,1,1,2,2-pentafluoroethyl iodide or hydrogen fluoride from a mixture containing 1,1,1,2,2-pentafluoroethyl iodide and hydrogen fluoride, comprising conducting a liquid—liquid separation of the distillate obtained through the top of a distillation column by the method as defined above in claim 2, and distilling a layer of 1,1,1,2,2-pentafluoroethyl iodide or a layer of hydrogen fluoride so that an azeotropic mixture of 1,1,1,2,2-pentafluoroethyl iodide and hydrogen fluoride is removed through the top of a distillation column while 1,1,1,2,2-pentafluoroethyl iodide or hydrogen fluoride is obtained from the bottom of the distillation column.

* * * * *